(12) United States Patent
Toda

(10) Patent No.: US 6,755,082 B2
(45) Date of Patent: Jun. 29, 2004

(54) DEVICE FOR MEASURING SOUND VELOCITY IN MATERIAL

(76) Inventor: Kohji Toda, 1-49-18 Futaba, Yokosuka (JP), 239-0814

( * ) Notice: Subject to any disclaimer, the term of this patent is extended or adjusted under 35 U.S.C. 154(b) by 143 days.

(21) Appl. No.: 10/153,566

(22) Filed: May 20, 2002

(65) Prior Publication Data

US 2003/0213304 A1 Nov. 20, 2003

(51) Int. Cl.[7] ............................................. G01N 29/18
(52) U.S. Cl. ......................................... 73/597; 600/448
(58) Field of Search .................. 73/597, 627, 64.53; 600/437, 448; 310/334, 335, 336

(56) References Cited

U.S. PATENT DOCUMENTS 5,211,059 A * 5/1993 Hayakawa et al. ........... 73/626
6,640,631 B1 * 11/2003 Toda .............................. 73/597

* cited by examiner

Primary Examiner—John E. Chapman

(57) ABSTRACT

A device for measuring sound velocity in material comprises a piezoelectric substrate, first- and second comb-shaped electrodes, a counter electrode, and a reflector. When input electric signals with a frequency f, respectively, are applied between the first comb-shaped electrode and the counter electrode in turn, longitudinal waves are radiated into a material existing between the counter electrode and the reflector, and then, reflected at the reflector, and after all, detected between the second comb-shaped electrode and the counter electrode as delayed electric signals $D_i$ in accordance with distances $Z_i$ between the counter electrode and the reflector. Electrical coupled-signals from the input electric signals and the delayed electric signals $D_i$ interfere respectively, so that respective interference signals $R_i$ occur. A sound velocity V in the material is estimated from the frequency f and the interference signals $R_i$.

17 Claims, 13 Drawing Sheets finger overlap-zone finger overlap-zone

DEVICE FOR MEASURING SOUND VELOCITY IN MATERIAL

BACKGROUND OF THE INVENTION

1. Field of the Invention.

The present invention relates to a device for measuring a sound velocity in material by means of using a piezoelectric substrate, an interdigital arrangement of two comb-shaped electrodes formed on an upper end surface of the piezoelectric substrate, a counter electrode formed on a lower end surface of the piezoelectric substrate, a distance adjusting system, a reflector, and a signal analyzer.

2. Description of the Prior Art.

Ultrasonic techniques for measuring the sound velocity in a liquid are essential, of late years, in the field of physical acoustics, industry, physical chemistry, biophysics, medical science, and others. A thickness mode piezoelectric transducer with parallel plate-like electrodes is commonly used for this purpose. Separating a delayed electric signal from an input electric signal is necessary for such a conventional type of transducer, because the conventional type of transducer is used both as input- and output electrodes. Thus, such the conventional type of transducer has a difficulty in quick response measurement, and a complicated circuit-construction.

On the other hand, an interdigital transducer on the piezoelectric substrate operates at a liquid-solid boundary as a leaky wave transducer for bulk wave radiation into the liquid. The leaky SAW traveling on a sufficiently thick substrate compared with the wavelength has only one mode without velocity dispersion. Such the interdigital transducer for the leaky SAW has a difficulty in making the radiation angle vertical, so that has a difficulty in use and measurement accuracy.

SUMMARY OF THE INVENTION

An object of the present invention is to provide a device for measuring a sound velocity in material capable of making an interdigital transducer act as a thickness mode transducer.

Another object of the present invention is to provide a device for measuring a sound velocity in material operating with a quick response.

Another object of the present invention is to provide a device for measuring a sound velocity in material need not a circulator, and so on.

Another object of the present invention is to provide a device for measuring a sound velocity in material capable of making the radiation angle vertical.

Another object of the present invention is to provide a device for measuring a sound velocity in material capable of low electric power consumption.

Another object of the present invention is to provide a device for measuring a sound velocity in material capable of measuring the sound velocity in cellular tissue.

Another object of the present invention is to provide a device for measuring a sound velocity in material excellent in durability and manufacturing.

Another object of the present invention is to provide a device for measuring a sound velocity in material, which is not affected by a change in circumstances, for example, a change in temperature.

A still other object of the present invention is to provide a device for measuring a sound velocity in material easy in use and having a small size which is very light in weight and has a simple structure.

According to one aspect of the present invention there is provided a device for measuring a sound velocity in material comprising a piezoelectric substrate, first- and second comb-shaped electrodes formed on an upper end surface of the piezoelectric substrate, a counter electrode formed on a lower end surface of the piezoelectric substrate, a reflector parallel with the lower end surface of the piezoelectric substrate, a distance adjusting system, and a signal analyzer. The counter electrode is in contact with a surface-part of a material. The reflector is in contact with the opposite surface-part of the material. The distance adjusting system adjusts distances $Z_i$ (i=1, 2, ..., n) between the surface-part and the opposite surface-part of the material in turn. The first- and second comb-shaped electrodes form an interdigital arrangement.

If input electric signals with a frequency f, respectively, are applied between the first comb-shaped electrode and the counter electrode in turn, longitudinal waves along the direction vertical to the lower end surface of the piezoelectric substrate are radiated into the material. The longitudinal waves are reflected at the reflector. Reflected longitudinal waves are detected between the second comb-shaped electrode and the counter electrode as delayed electric signals $D_i$ (i=1, 2, ..., n) in accordance with the distances $Z_i$. On the other hand, electrical coupled-signals from the input electric signals are also detected between the second comb-shaped electrode and the counter electrode. The electrical coupled-signals and the delayed electric signals $D_i$ interfere respectively with each other, so that respective interference signals $R_i$ (i=1, 2, ..., n) occur. Tracing a dependence of respective amplitudes of the interference signals $R_i$ on the distances $Z_i$ provides a distance periodicity $\Delta Z$. Thus, a sound velocity V in the material is calculated from the product of twice the frequency f and the distance periodicity $\Delta Z$, that is, $V=2f\Delta Z$.

According to another aspect of the present invention there is provided a device for measuring a sound velocity in material, wherein the ratio of the interdigital periodicity of the interdigital arrangement to the thickness of the piezoelectric substrate is smaller than four times the ratio of the longitudinal wave velocity in the material to the longitudinal wave velocity in the piezoelectric substrate.

According to another aspect of the present invention there is provided a device for measuring a sound velocity in material, wherein increasing the number of electrode-finger pairs in the interdigital arrangement makes the directionality of the longitudinal waves sharper under a condition that the total amount of all the finger-areas of the first comb-shaped electrode is constant.

According to another aspect of the present invention there is provided a piezoelectric substrate made of a piezoelectric ceramic plate, the polarization axis thereof being parallel to the thickness direction thereof.

According to another aspect of the present invention there is provided a device for measuring a sound velocity in material, wherein the material is a liquid matter.

According to another aspect of the present invention there is provided a device for measuring a sound velocity in material, wherein the material is a cellular tissue.

According to another aspect of the present invention there is provided a device for measuring a sound velocity in material further comprising a polymer film, with which the lower end surface of the counter electrode is coated.

According to another aspect of the present invention there is provided a device for measuring a sound velocity in material further comprising a silicone rubber, with which the lower end surface of the counter electrode is coated.

According to another aspect of the present invention there is provided a device for measuring a sound velocity in material comprising a first piezoelectric substrate, a first interdigital arrangement of two comb-shaped electrodes formed on a lower end surface of the first piezoelectric substrate, a second piezoelectric substrate, a second interdigital arrangement of two comb-shaped electrodes formed on an upper end surface of the second piezoelectric substrate, a counter electrode cemented between the first- and second piezoelectric substrates, a reflector parallel with the lower end surface of the first piezoelectric substrate, a distance adjusting system, and a signal analyzer. A lower end surface of the first interdigital arrangement is in contact with a surface-part of a material. The reflector is in contact with the opposite surface-part of the material. The distance adjusting system adjusts distances $Z_i$ (i=1, 2, ..., n) between the surface-part and the opposite surface-part of the material in turn.

If input electric signals with a frequency f, respectively, are applied between one of the two comb-shaped electrodes in the first interdigital arrangement and the counter electrode, longitudinal waves along the direction vertical to the lower end surface of the first piezoelectric substrate are radiated into the material. The longitudinal waves are reflected at the reflector. Reflected longitudinal waves are detected between one of the two comb-shaped electrodes in the second interdigital arrangement and the counter electrode as delayed electric signals $D_i$ (i=1, 2, ..., n) in accordance with the distances $Z_i$. On the other hand, electrical coupled-signals from the input electric signals are also detected between the one of the two comb-shaped electrodes in the second interdigital arrangement and the counter electrode. The electrical coupled-signals and the delayed electric signals $D_i$ interfere respectively with each other, so that respective interference signals $R_i$ (i=1, 2, ..., n) occur. Tracing a dependence of respective amplitudes of the interference signals $R_i$ on the distances $Z_i$ provides a distance periodicity $\Delta Z$. Thus, a sound velocity V in the material is calculated from the product of twice the frequency f and the distance periodicity $\Delta Z$, that is, $V=2f\Delta Z$.

According to another aspect of the present invention there is provided a device for measuring a sound velocity in material, wherein the finger direction of the second interdigital arrangement is orthogonal to that of the first interdigital arrangement.

According to another aspect of the present invention there is provided a device for measuring a sound velocity in material, wherein the finger width in the one of the two comb-shaped electrodes in the first interdigital arrangement is wider than that in the other of the two comb-shaped electrodes in the first interdigital arrangement, and the finger width in the one of the two comb-shaped electrodes in the second interdigital arrangement is wider than that in the other of the two comb-shaped electrodes in the second interdigital arrangement.

According to another aspect of the present invention there is provided a device for measuring a sound velocity in material, wherein the ratio of the interdigital periodicity of the first interdigital arrangement to the thickness of the first piezoelectric substrate is smaller than four times the ratio of the longitudinal wave velocity in the material to the longitudinal wave velocity in the first piezoelectric substrate.

According to another aspect of the present invention there is provided a device for measuring a sound velocity in material, wherein increasing the number of electrode-finger pairs in the first interdigital arrangement makes the directionality of the longitudinal waves sharper under a condition that the total amount of all the finger-areas of the one of the two comb-shaped electrodes in the first interdigital arrangement is constant.

According to another aspect of the present invention there is provided a device for measuring a sound velocity in material comprising a first piezoelectric substrate, a first comb-shaped electrode formed on a lower end surface of the first piezoelectric substrate, a second piezoelectric substrate, a second comb-shaped electrode formed on an upper end surface of the second piezoelectric substrate, a counter electrode cemented between the first- and second piezoelectric substrates, a reflector parallel with the lower end surface of the first piezoelectric substrate, a distance adjusting system, and a signal analyzer. A lower end surface of the first comb-shaped electrode is in contact with a surface-part of a material. The reflector is in contact with the opposite surface-part of the material. The distance adjusting system adjusts distances $Z_i$ (i=1, 2, ..., n) between the surface-part and the opposite surface-part of the material in turn.

If input electric signals with a frequency f, respectively, are applied between the first comb-shaped electrode and the counter electrode, longitudinal waves along the direction vertical to the lower end surface of the first piezoelectric substrate are radiated into the material. The longitudinal waves are reflected at the reflector. Reflected longitudinal waves are detected between the second comb-shaped electrode and the counter electrode as delayed electric signals $D_i$ (i=1, 2, ..., n) in accordance with the distances $Z_i$. On the other hand, electrical coupled-signals from the input electric signals are also detected between the second comb-shaped electrode and the counter electrode. The electrical coupled-signals and the delayed electric signals $D_i$ interfere respectively with each other, so that respective interference signals $R_i$ (i=1, 2, ..., n) occur. Tracing a dependence of respective amplitudes of the interference signals $R_i$ on the distances $Z_i$ provides a distance periodicity $\Delta Z$. Thus, a sound velocity V in the material is calculated from the product of twice the frequency f and the distance periodicity $\Delta Z$, that is, $V=2f\Delta Z$.

According to another aspect of the present invention there is provided a device for measuring a sound velocity in material, wherein the finger direction of the second comb-shaped electrode is orthogonal to that of the first comb-shaped electrode.

According to other aspect of the present invention there is provided a device for measuring a sound velocity in material, wherein the ratio of the interdigital periodicity of the first comb-shaped electrode to the thickness of the first piezoelectric substrate is smaller than four times the ratio of the longitudinal wave velocity in the material to the longitudinal wave velocity in the first piezoelectric substrate.

According to a further aspect of the present invention there is provided a device for measuring a sound velocity in material, wherein increasing the number of electrode-finger pairs in the first comb-shaped electrode makes the directionality of the longitudinal waves sharper under a condition that the total amount of all the finger-areas of the first comb-shaped electrode is constant.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
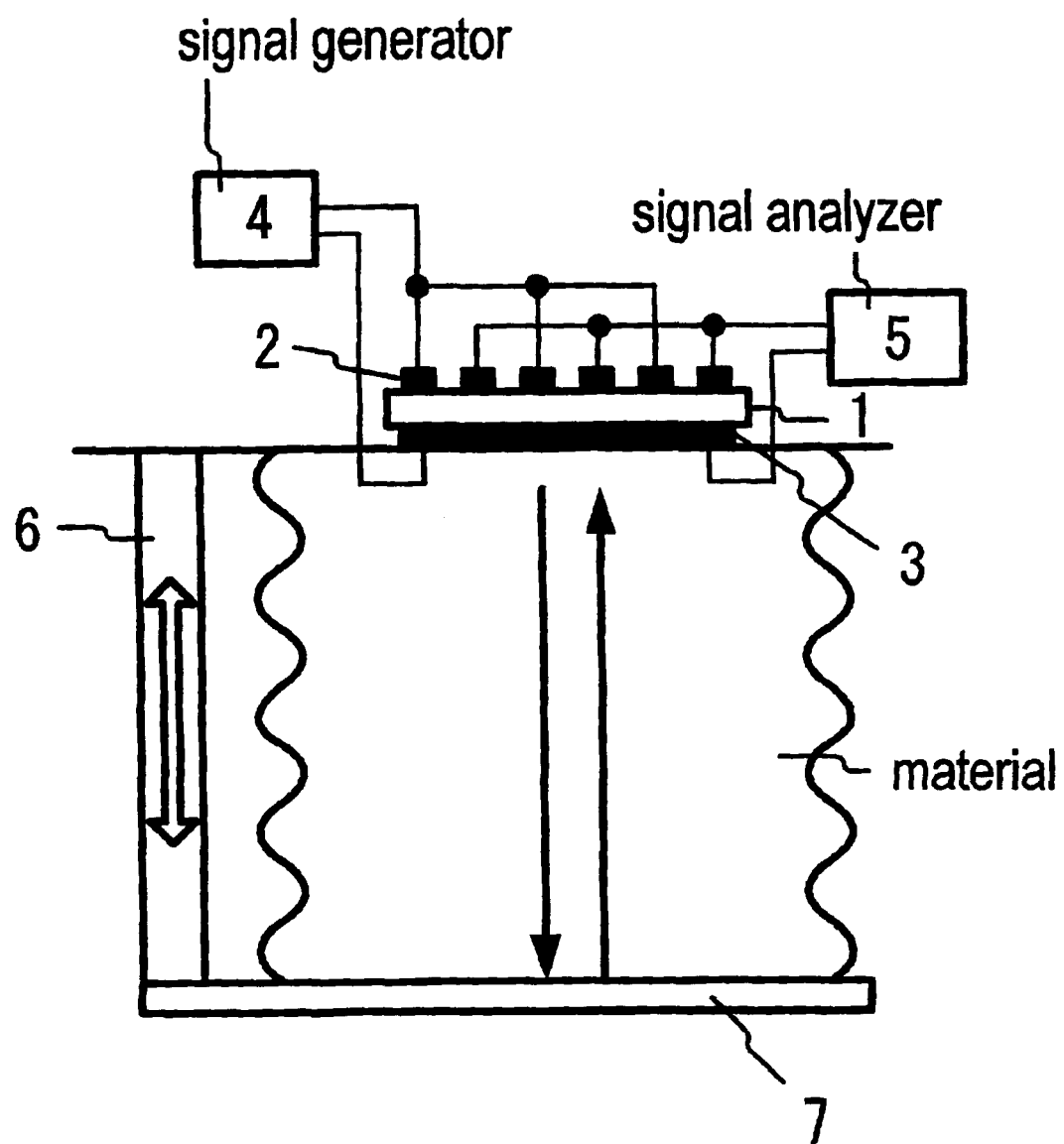
FIG. 1 shows a schematic illustration of a device for measuring sound velocity in material according to a first embodiment of the present invention.

FIG. 1 shows a schematic illustration of a device for measuring sound velocity in material according to a first embodiment of the present invention. The device for measuring sound velocity in material comprises piezoelectric substrate 1, interdigital arrangement 2 of two comb-shaped electrodes (2A and 2B), counter electrode 3, signal generator 4, signal analyzer 5, distance adjusting system 6, and reflector 7. Piezoelectric substrate 1 is made of a piezoelectric ceramic plate with a thickness (T) of 500 µm, and the polarization axis thereof is parallel to the thickness direction thereof. Interdigital arrangement 2, made of an aluminum thin film, is formed on an upper end surface of piezoelectric substrate 1. Counter electrode 3, made of an aluminum thin film, is formed on a lower end surface of piezoelectric substrate 1, and in contact with a surface-part of a material. Reflector 7 is arranged to be parallel with the lower end surface of piezoelectric substrate 1, and in contact with the opposite surface-part of the material. Distance adjusting system 6 changes the distance between the surface-part and the opposite surface-part of the material gradually. Thus, the device for measuring sound velocity in material in FIG. 1 has a small size, which is very light in weight and has a simple structure.

Figure 2:
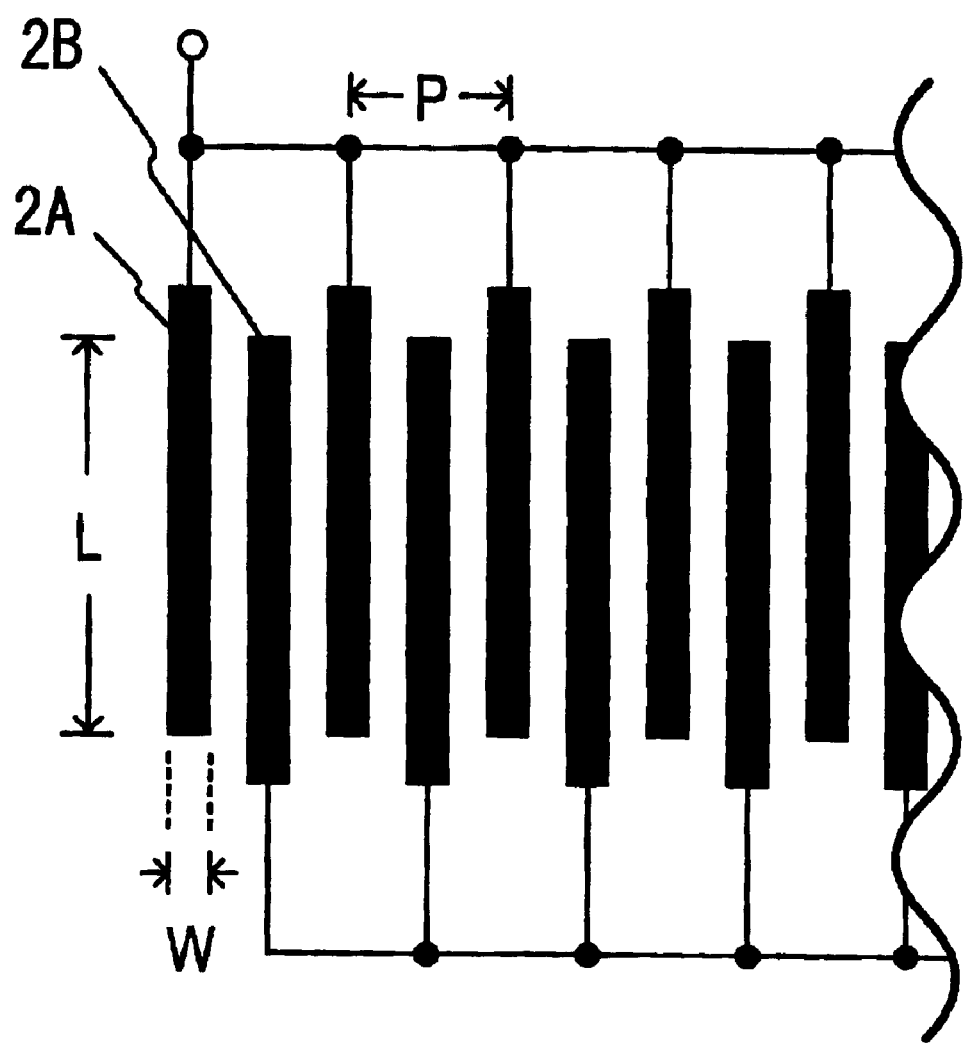
FIG. 2 shows a fragmentary top plan view of interdigital arrangement 2.

FIG. 2 shows a fragmentary top plan view of interdigital arrangement 2. Interdigital arrangement 2 has fifteen electrode-finger pairs, a finger-overlap length (L) of 5 mm, a finger width (W) of 75 µm, and an interdigital periodicity (P) of 300 µm. Interdigital arrangement 2 is composed of first comb-shaped electrode 2A and second comb-shaped electrode 2B.

In the device for measuring sound velocity in material in FIG. 1, if input electric signals with a frequency f, respectively, are applied between first comb-shaped electrode 2A and counter electrode 3 from signal generator 4 in turn, longitudinal waves along the direction vertical to the lower end surface of piezoelectric substrate 1 are radiated into the material through a surface-part of the material.

If the material is water, the longitudinal wave velocity in water ($V_w$) is approximately 1,500 m/s. On the other hand, the longitudinal wave velocity in piezoelectric substrate 1 ($V_s$) is 4,500 m/s. Thus, the ratio of the $V_w$ value to the $V_s$ value, that is 1,500/4,500, is approximately 0.333. The ratio of the interdigital periodicity (P) of interdigital arrangement 2 to the thickness (T) of piezoelectric substrate 1, that is 300/500, is 0.6, which is still smaller than four times the ratio of the $V_w$ value to the $V_s$ value. Under such a condition of $P/T<4V_w/V_s$, the longitudinal waves along the direction vertical to the lower end surface of piezoelectric substrate 1 are effectively radiated into water. In the same way, the longitudinal waves are effectively radiated into, for example, a cellular tissue.

The longitudinal waves radiated into the material are reflected at reflector 7. In this time, a distance between the surface-part and the opposite surface-part of the material is changed gradually by distance adjusting system 6. In other words, distance adjusting system 6 adjusts distances $Z_i$ (i=1, 2, . . . , n) between the surface-part and the opposite surface-part of the material in turn. Thus, reflected longitudinal waves are detected between second comb-shaped electrode 2B and counter electrode 3 as delayed electric signals $D_i$ (i=1, 2, . . . , n) in accordance with the distances $Z_i$. On the other hand, electrical coupled-signals from the input electric signals are also detected between second comb-shaped electrode 2B and counter electrode 3. The electrical coupled-signals and the delayed electric signals $D_i$ interfere respectively with each other, so that respective interference signals $R_i$ (i=1, 2, . . . , n) are detected at signal analyzer 5. Tracing a dependence of respective amplitudes of the interference signals $R_i$ on the distances $Z_i$ provides a distance periodicity $\Delta Z$. Thus, a sound velocity V in the material is calculated from the product of twice the frequency f and the distance periodicity $\Delta Z$, that is, $V=2f\Delta Z$.

Figure 3:
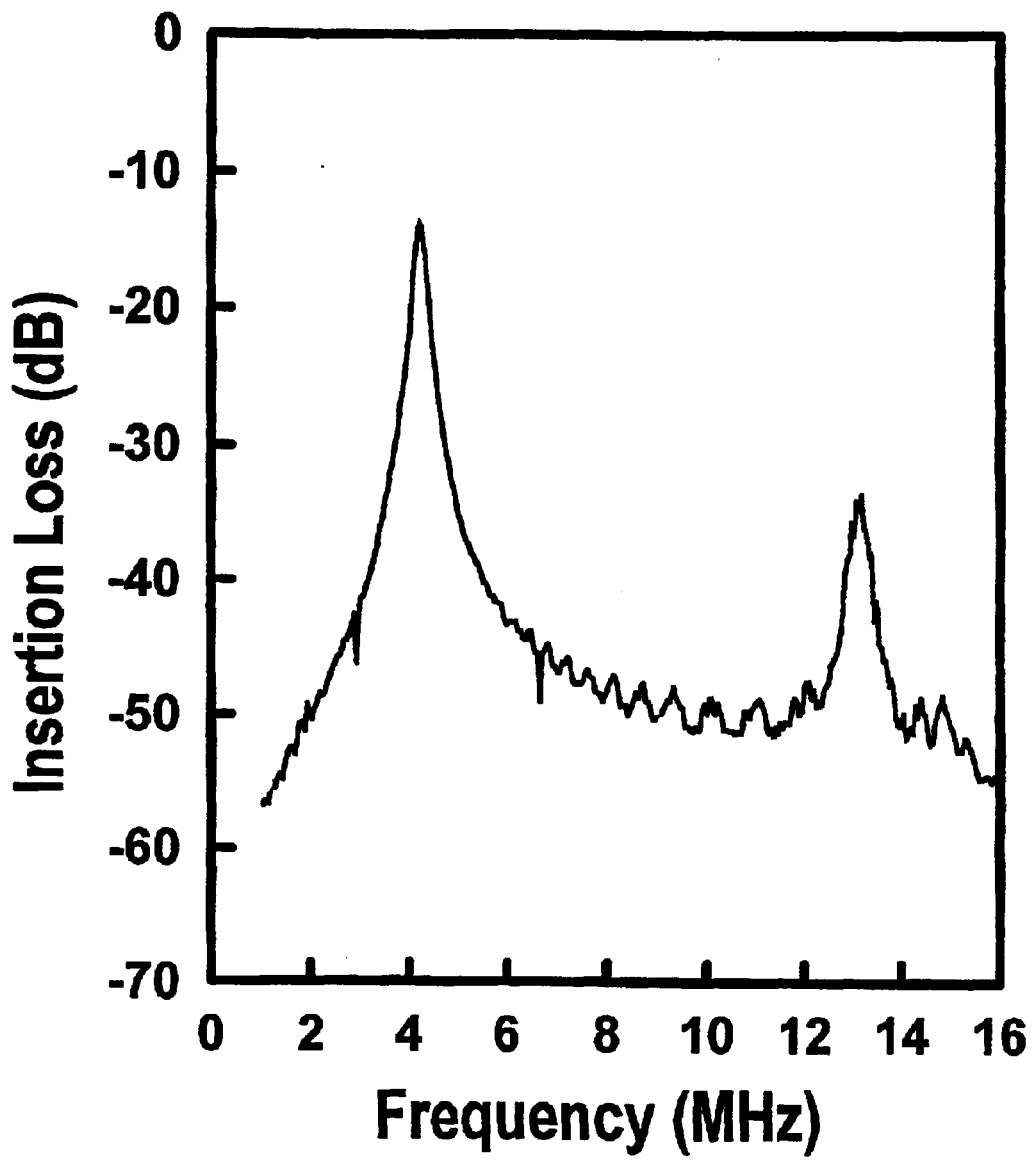
FIG. 3 shows a relationship between the insertion loss and the frequency of the input electric signal applied to the device for measuring sound velocity in material in FIG. 1.

FIG. 3 shows a relationship between the insertion loss and the frequency of the input electric signal applied to the device for measuring sound velocity in material in FIG. 1 having the distance of 5 cm between the surface-part and the opposite surface-part of the material. It is clear that the insertion loss is smallest at approximately 4.2 MHz.

Figure 4:
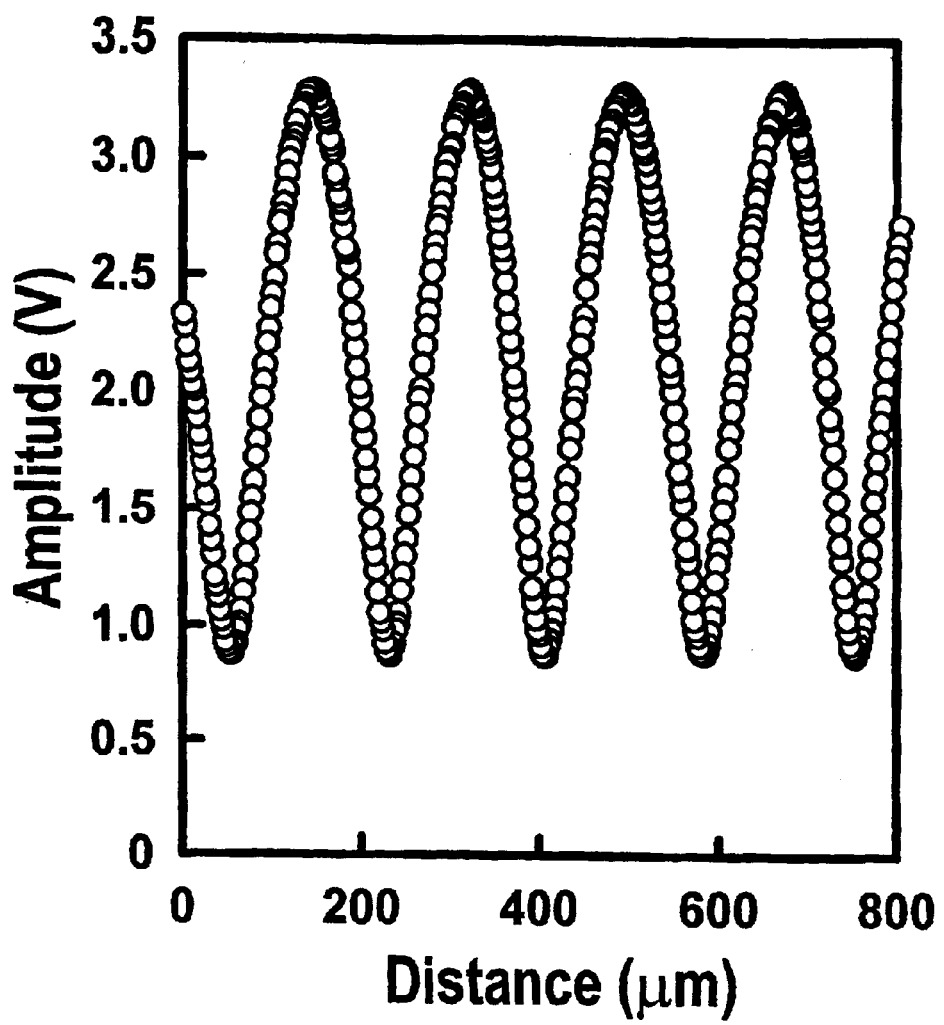
FIG. 4 shows a relationship between the amplitude of the interference signal $R_i$ and the distance $Z_i$ in the device for measuring sound velocity in material in FIG. 1.

FIG. 4 shows a relationship between the amplitude of the interference signal $R_i$ and the distance $Z_i$ in the device for measuring sound velocity in material in FIG. 1 operated at the frequency of 4.2 MHz. It is noticed that the amplitude of the interference signal $R_i$ is periodically dependent on the distance $Z_i$. A distance between two neighboring peak amplitudes corresponds to the distance periodicity $\Delta Z$.

Figure 5:
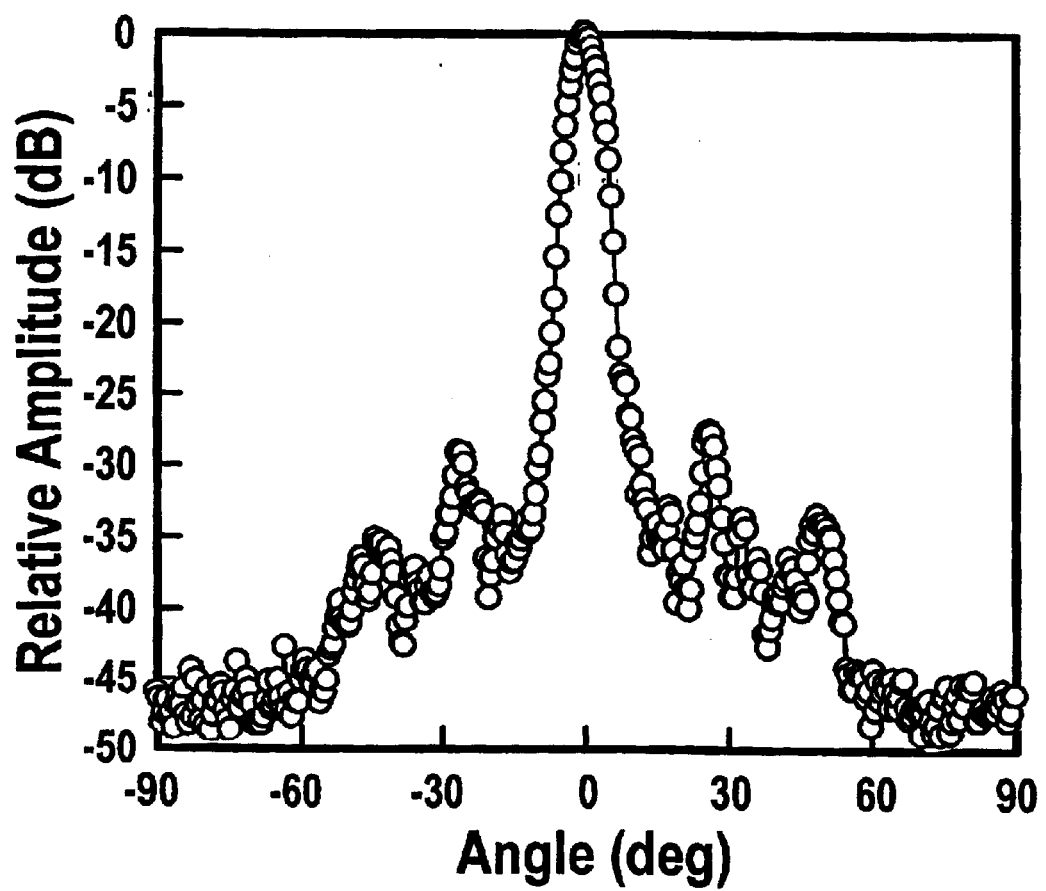
FIG. 5 shows a relationship between the relative amplitude and the radiation angle of the longitudinal waves into water from the device for measuring sound velocity in material in FIG. 1.

FIG. 5 shows a relationship between the relative amplitude and the radiation angle of the longitudinal waves into water from the device for measuring sound velocity in material in FIG. 1. It seems that there exists only the main lobe, because any grating lobe is suppressed. As a result, the use of interdigital arrangement 2 enables only a vertical radiation to the lower end surface of piezoelectric substrate 1 into water. Thus, the longitudinal waves are effectively radiated into, for example, a cellular tissue through a skin, along a vertical direction to the lower end surface of piezoelectric substrate 1.

Figure 6:
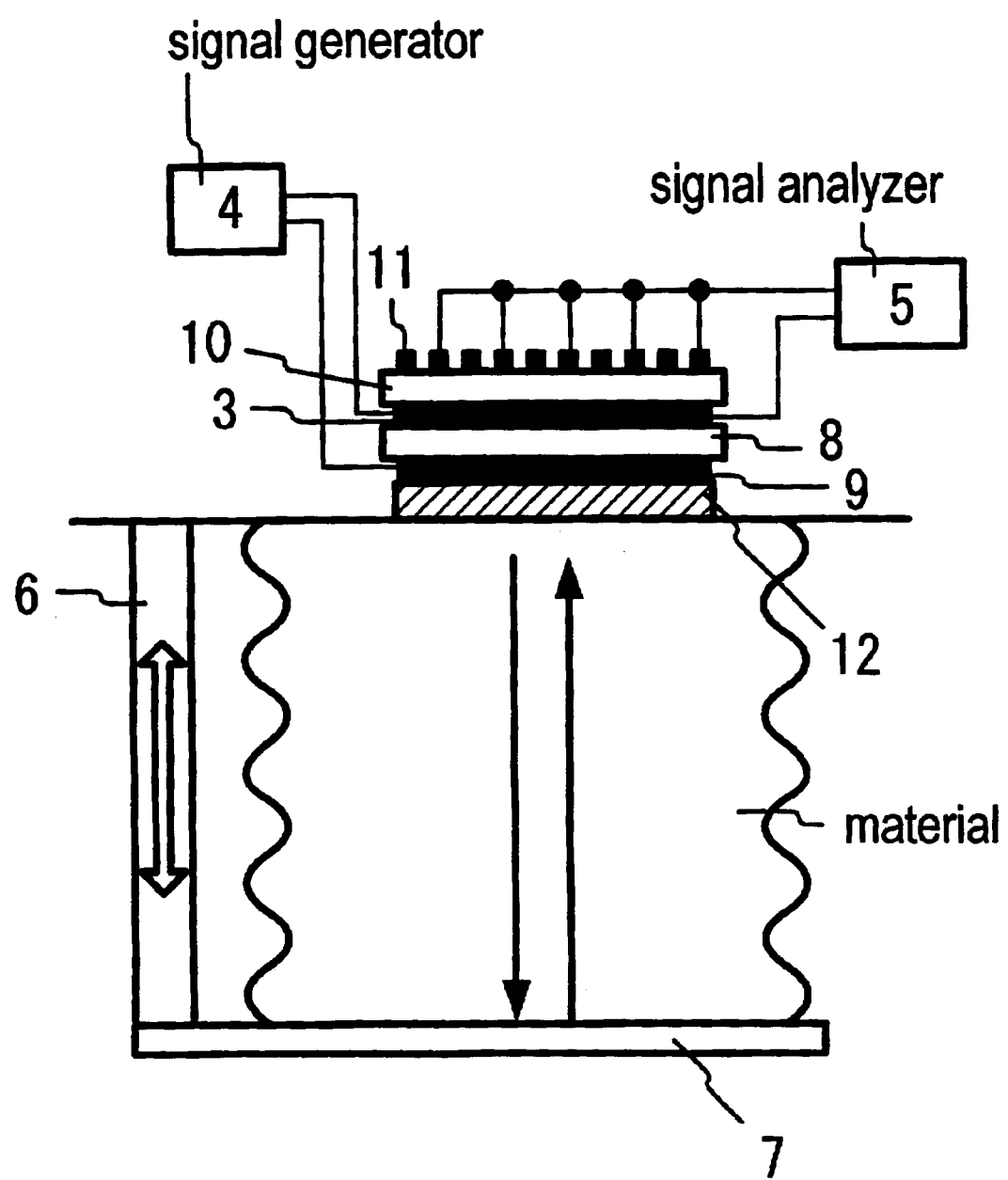
FIG. 6 shows a schematic illustration of a device for measuring sound velocity in material according to a second embodiment of the present invention.

FIG. 6 shows a schematic illustration of a device for measuring sound velocity in material according to a second embodiment of the present invention. The device for measuring sound velocity in material comprises first piezoelectric substrate 8, first interdigital arrangement 9 of two comb-shaped electrodes (9A and 9B), second piezoelectric substrate 10, second interdigital arrangement 11 of two comb-shaped electrodes (11A and 11B), silicone rubber 12, counter electrode 3, signal generator 4, signal analyzer 5, distance adjusting system 6, and reflector 7. Second interdigital arrangement 11 is formed on the upper end surface of second piezoelectric substrate 10. Counter electrode 3 is cemented between first piezoelectric substrate 8 and second piezoelectric substrate 10, which are made of the same materials as piezoelectric substrate 1, and have the same sizes as piezoelectric substrate 1. First interdigital arrangement 9 is formed on a lower end surface of first piezoelectric substrate 8. The lower end surface of first interdigital arrangement 9 is coated with silicone rubber 12, which is in contact with a surface-part of a material.

Figure 7:
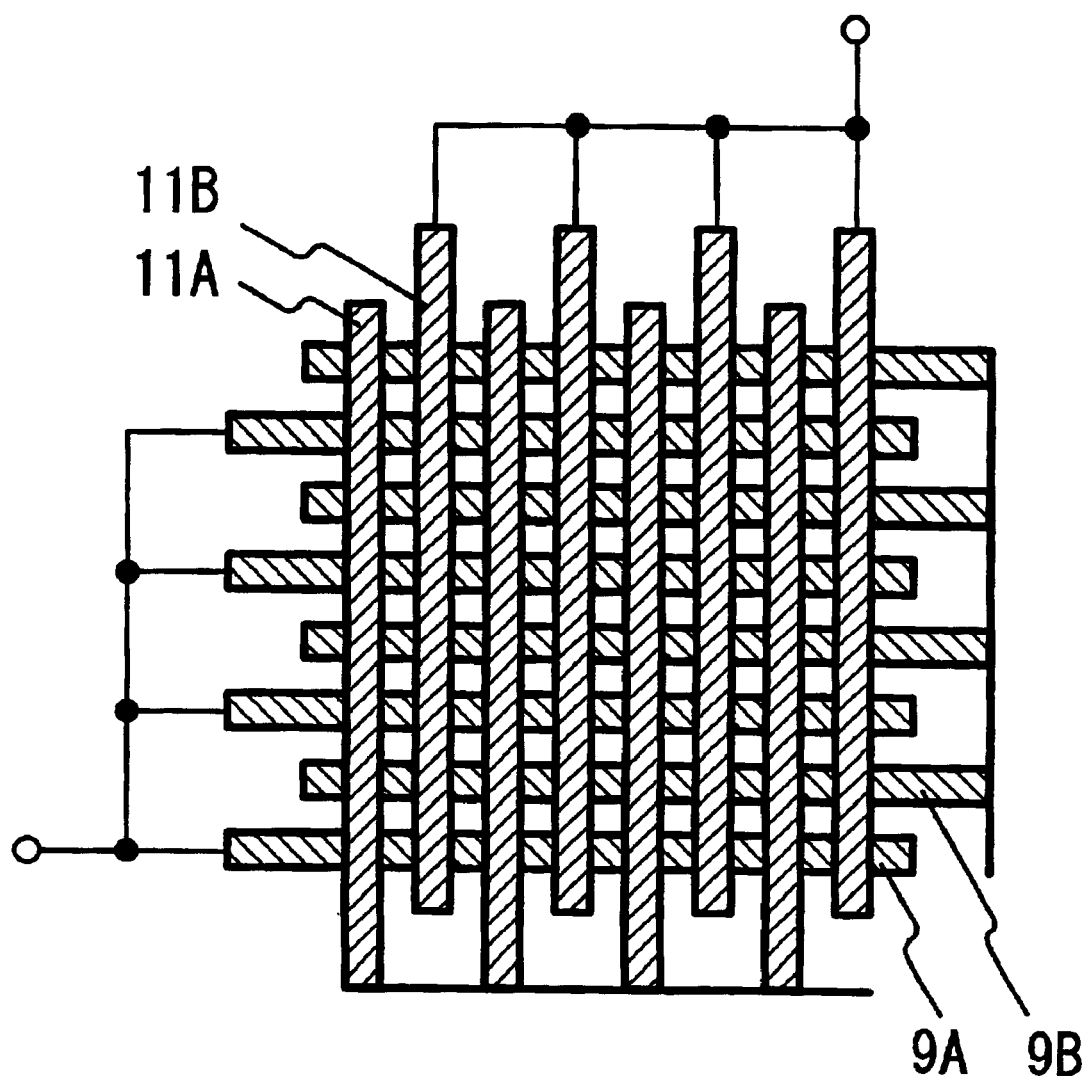
FIG. 7 shows a schematic illustration of first interdigital arrangement 9 and second interdigital arrangement 11 in the device for measuring sound velocity in material in FIG. 6.

FIG. 7 shows a schematic illustration of first interdigital arrangement 9 composed of first comb-shaped electrode 9A and second comb-shaped electrode 9B, and second interdigital arrangement 11 composed of first comb-shaped electrode 11A and second comb-shaped electrode 11B in the device for measuring sound velocity in material in FIG. 6. First interdigital arrangement 9 and second interdigital arrangement 11, made of an aluminum thin film, respectively, have twenty electrode-finger pairs, a finger-overlap length (L) of 5 mm, a finger width (W) of 57 $\mu$m, and an interdigital periodicity (P) of 225 $\mu$m, respectively. The finger direction of first interdigital arrangement 9 and that of second interdigital arrangement 11 are orthogonal each other. First comb-shaped electrode 9A and second comb-shaped electrode 11B are connected with signal generator 4 and signal analyzer 5 in FIG. 6, respectively.

In the device for measuring sound velocity in material in FIG. 6, if input electric signals with a frequency f, respectively, are applied between first comb-shaped electrode 9A and counter electrode 3 from signal generator 4 in turn, longitudinal waves along the direction vertical to the lower end surface of first piezoelectric substrate 8 are radiated into the material through silicone rubber 12. When the material is water, the ratio of the $V_w$ value to the $V_s$ value is approximately 0.333, as mentioned above. On the other hand, the ratio of the interdigital periodicity (P) of interdigital arrangement 9 to the thickness (T) of first piezoelectric substrate 8, that is 225/500, is 0.45, which is still smaller than four times the ratio of the $V_w$ value to the $V_s$ value. Under such a condition of $P/T<4V_w/V_s$, the longitudinal waves along the direction vertical to the lower end surface of first piezoelectric substrate 8 are effectively radiated into water through silicone rubber 12. In addition, the directionality of the longitudinal waves is sharper than that of the longitudinal waves in FIG. 1. In other words, the smaller ratio P/T than the ratio $4V_w/V_s$, the sharper directionality.

The longitudinal waves radiated into the material are reflected at reflector 7. In this time, distance adjusting system 6 adjusts distances $Z_i$ (i=1, 2, . . . , n) between the surface-part and the opposite surface-part of the material in turn. Thus, reflected longitudinal waves are detected between second comb-shaped electrode 11B and counter electrode 3 as delayed electric signals $D_i$ (i=1, 2, . . . , n) in accordance with the distances $Z_i$. In this time, the directionality of the reflected longitudinal waves detected between second comb-shaped electrode 11B and counter electrode 3 is sharper than that of the reflected longitudinal waves detected between second comb-shaped electrode 2B and counter electrode 3 in FIG. 1, because the finger direction of first interdigital arrangement 9 is orthogonal to that of second interdigital arrangement 11.

On the other hand, electrical coupled-signals from the input electric signals applied between first comb-shaped electrode 9A and counter electrode 3 are also detected between second comb-shaped electrode 11B and counter electrode 3. The electrical coupled-signals and the delayed electric signals $D_i$ interfere respectively with each other, so that respective interference signals $R_i$ (i=1, 2, . . . , n) are detected at signal analyzer 5. Tracing a dependence of respective amplitudes of the interference signals $R_i$ on the distances $Z_i$ provides a distance periodicity $\Delta Z$. Thus, a sound velocity V in the material is calculated from the product of twice the frequency f and the distance periodicity $\Delta Z$, that is, $V=2f\Delta Z$. In addition, the sound velocity V is more precisely calculated than that in FIG. 1.

Figure 8:
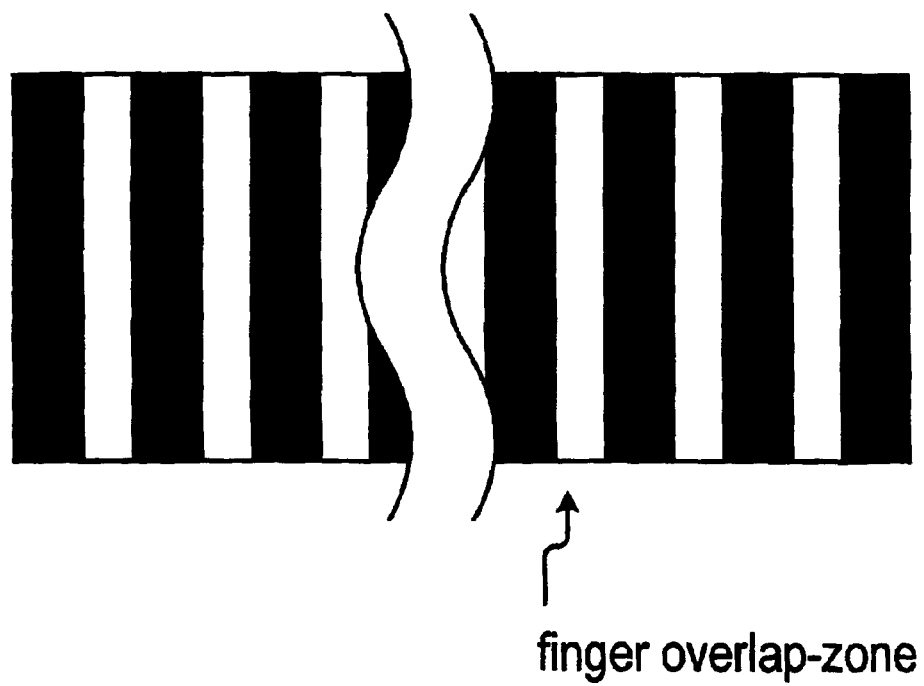
FIG. 8 shows a top plan view of the finger overlap-zone of interdigital arrangement 2.

FIG. 8 shows a top plan view of the finger overlap-zone of interdigital arrangement 2.

Figure 9:
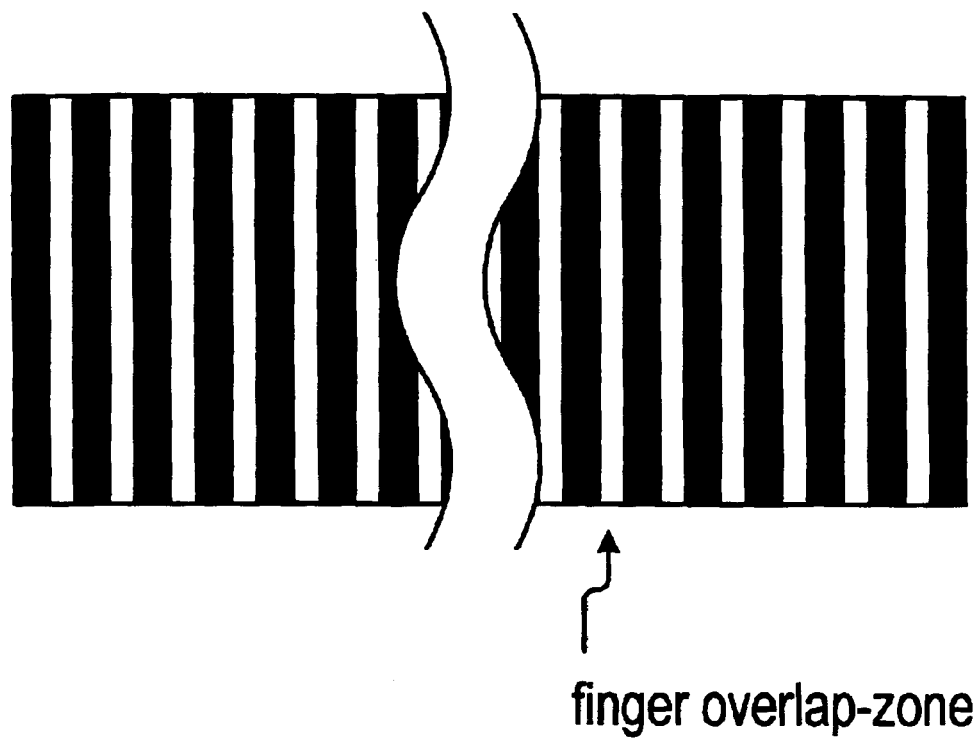
FIG. 9 shows a top plan view of the finger overlap-zone of first interdigital arrangement 9.

FIG. 9 shows a top plan view of the finger overlap-zone of first interdigital arrangement 9. The finger overlap-zone of first interdigital arrangement 9 and that of interdigital arrangement 2 are the same in size. In addition, the total amount of all the finger-areas of first comb-shaped electrode 9A is the same as that of first comb-shaped electrode 2A.

A comparison between FIGS. 8 and 9 indicates that first interdigital arrangement 9 and interdigital arrangement 2 are different from each other with respect to the number of electrode-finger pairs, the finger width (W), and the interdigital periodicity (P). Actually, the number of electrode-finger pairs in first interdigital arrangement 9 is 4/3 times that in interdigital arrangement 2. At the same time, the interdigital periodicity (P) of first interdigital arrangement 9 is approximately 3/4 times that of interdigital arrangement 2, and the finger width (W) of first interdigital arrangement 9 is also 3/4 times that of interdigital arrangement 2. It is recognized that the use of first interdigital arrangement 9 causes a sharper directionality of the longitudinal waves than interdigital arrangement 2. This means that increasing the number of electrode-finger pairs suppresses the grating lobes still more under a condition that the total amount of all the finger-areas of the first comb-shaped electrode is constant. As a result, the number of electrode-finger pairs has influence on the directionality of the longitudinal waves into a material under the condition that the total amount of all the finger-areas of the first comb-shaped electrode is constant.

Figure 10:
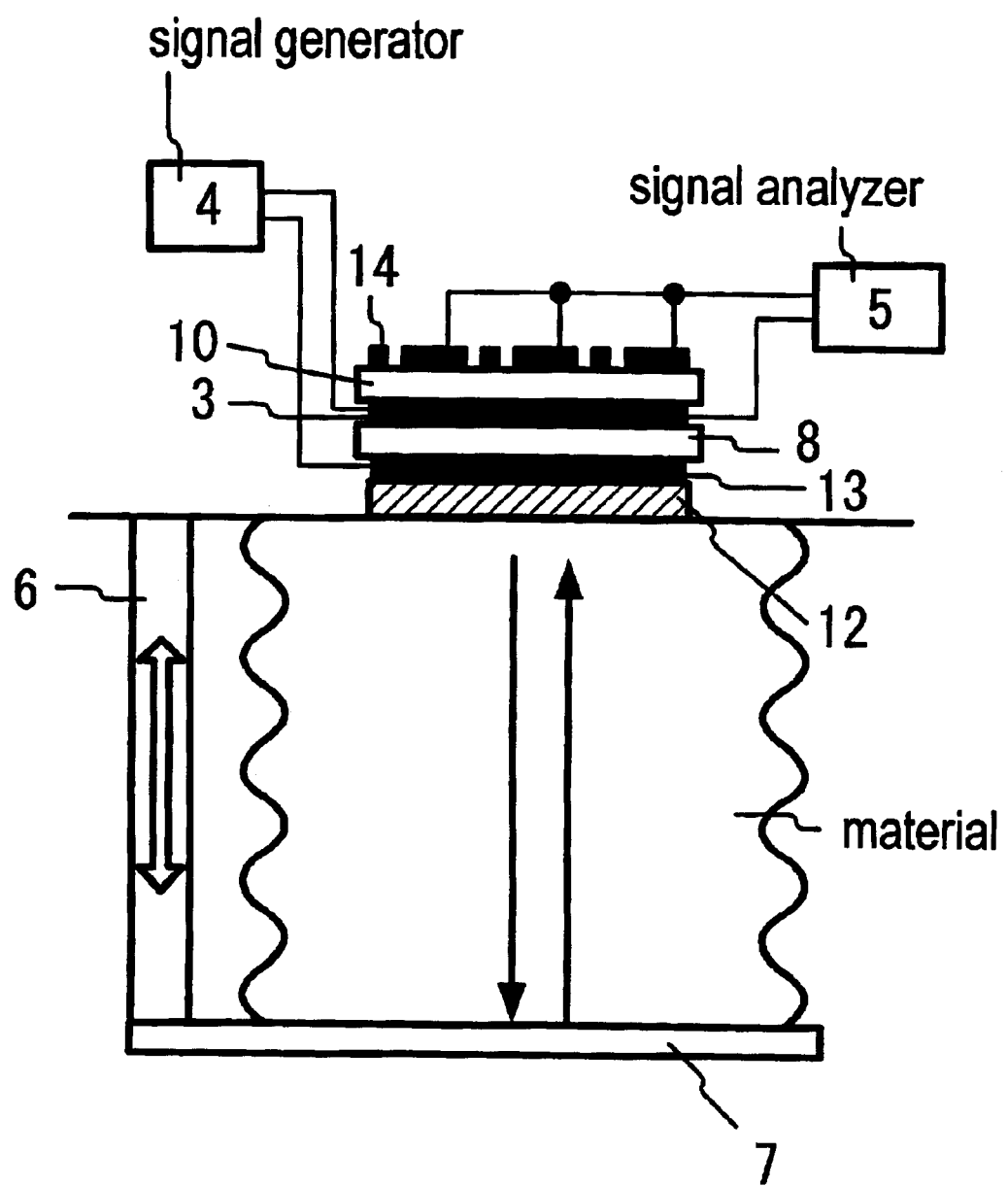
FIG. 10 shows a schematic illustration of a device for measuring sound velocity in material according to a third embodiment of the present invention.

FIG. 10 shows a schematic illustration of a device for measuring sound velocity in material according to a third embodiment of the present invention. The device for measuring sound velocity in material has the same construction as FIG. 6 except for the use of first interdigital arrangement 13 of two comb-shaped electrodes (13A and 13B) and second interdigital arrangement 14 of two comb-shaped electrodes (14A and 14B) in place of first interdigital arrangement 9 and second interdigital arrangement 11, respectively.

Figure 11:
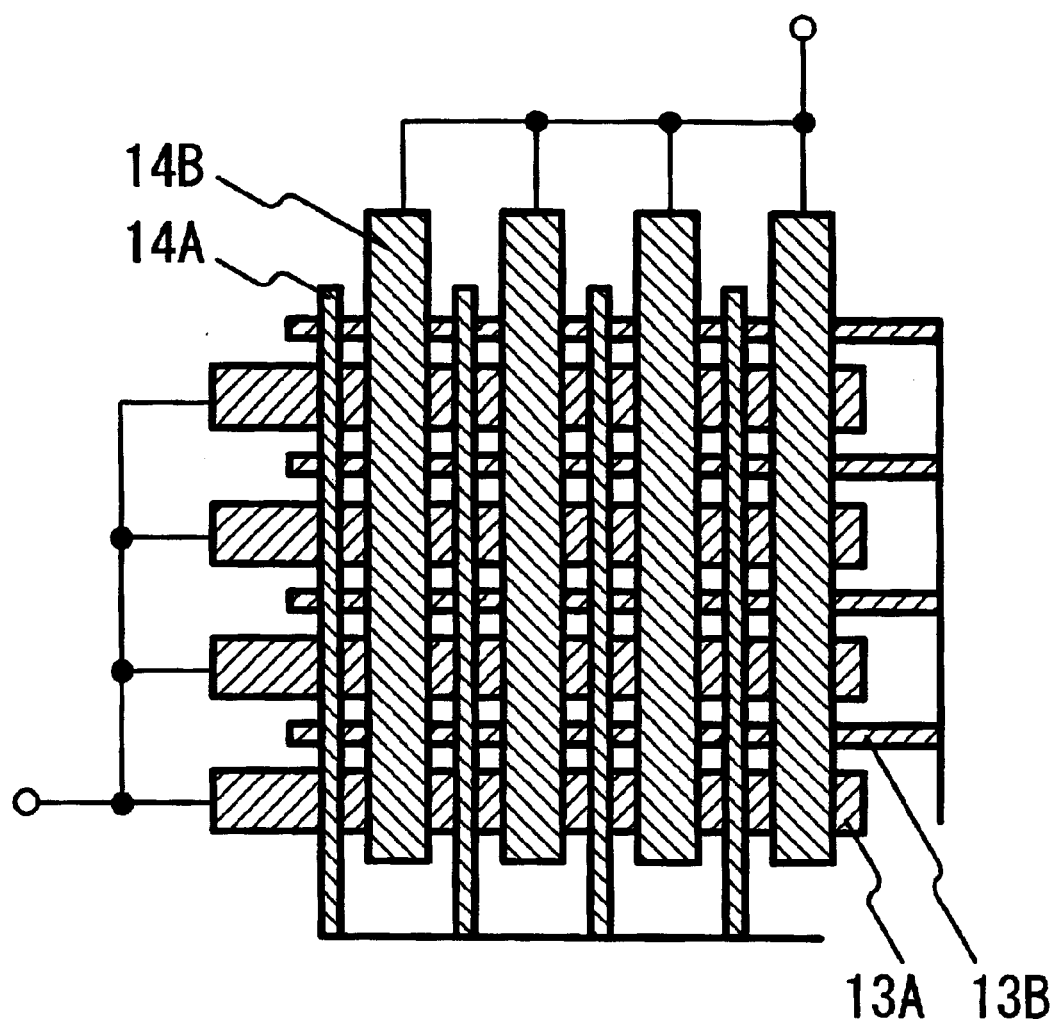
FIG. 11 shows a schematic illustration of first interdigital arrangement 13 and second interdigital arrangement 14 in the device for measuring sound velocity in material in FIG. 10.

FIG. 11 shows a schematic illustration of first interdigital arrangement 13 composed of first comb-shaped electrode 13A and second comb-shaped electrode 13B, and second interdigital arrangement 14 composed of first comb-shaped electrode 14A and second comb-shaped electrode 14B in the device for measuring sound velocity in material in FIG. 10.

The finger direction of first interdigital arrangement 13 is orthogonal to that of second interdigital arrangement 14. First interdigital arrangement 13, made of an aluminum thin film, has twenty electrode-finger pairs, a finger-overlap length (L) of 5 mm, and an interdigital periodicity (P) of 225 μm. First comb-shaped electrode 13A has a finger width ($W_A$) of 45 μm, and second comb-shaped electrode 13B has a finger width ($W_B$) of 12 μm. Second interdigital arrangement 14 is made of the same material and has the same construction pattern as first interdigital arrangement 13 except that first comb-shaped electrode 14A has a finger width ($W_A$) of 12 μm, and second comb-shaped electrode 14B has a finger width ($W_B$) of 45 μm. First comb-shaped electrode 13A and second comb-shaped electrode 14B are connected with function generator 4 and signal analyzer 5 in FIG. 10, respectively.

In the device for measuring sound velocity in material in FIG. 10, if input electric signals with a frequency f, respectively, are applied between first comb-shaped electrode 13A and counter electrode 3 from signal generator 4 in turn, longitudinal waves along the direction vertical to the lower end surface of first piezoelectric substrate 8 are radiated into the material through silicone rubber 12. When the material is water, the condition of $P/T<4V_w/V_s$ enables a radiation of the longitudinal waves along the direction vertical to the lower end surface of first piezoelectric substrate 8 into water. In addition, the directionality of the longitudinal waves is sharper than that of the longitudinal waves in FIG. 6. In other words, a condition of $W_A/W_B$ in first interdigital arrangement 13 makes the directionality of the longitudinal waves sharper.

If the longitudinal waves are reflected at reflector 7 as shown in FIG. 10, reflected longitudinal waves are detected between second comb-shaped electrode 14B and counter electrode 3 as the delayed electric signals $D_i$ in accordance with the distances $Z_i$, respectively. In this time, the directionality of the reflected longitudinal waves is sharper than that of the longitudinal waves radiated into the material, because the finger direction of first interdigital arrangement 13 is orthogonal to that of second interdigital arrangement 14.

On the other hand, electrical coupled-signals from the input electric signals applied between first comb-shaped electrode 13A and counter electrode 3 are also detected between second comb-shaped electrode 14B and counter electrode 3. The electrical coupled-signals and the delayed electric signals $D_i$ interfere respectively with each other, so that the respective interference signals $R_i$ are detected at signal analyzer 5. Tracing a dependence of respective amplitudes of the interference signals $R_i$ on the distances $Z_i$ provides a distance periodicity ΔZ. Thus, a sound velocity V in the material is calculated from the product of twice the frequency f and the distance periodicity ΔZ, that is, V=2fΔZ. In addition, the sound velocity V is more precisely estimated than that in FIG. 6.

Figure 12:
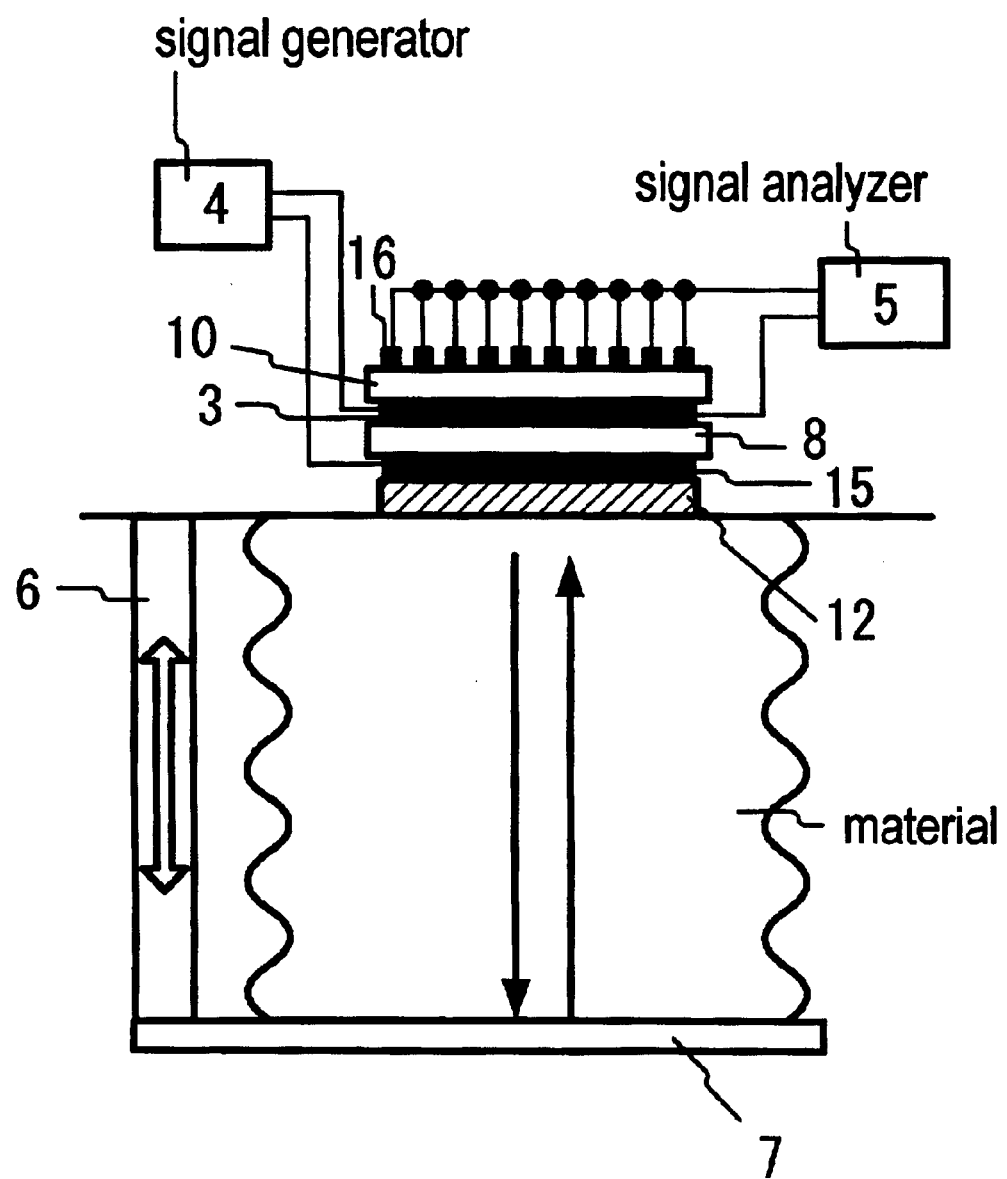
FIG. 12 shows a schematic illustration of a device for measuring sound velocity in material according to a fourth embodiment of the present invention.

FIG. 12 shows a schematic illustration of a device for measuring sound velocity in material according to a fourth embodiment of the present invention. The device for measuring sound velocity in material has the same construction as FIG. 6 except for the use of first comb-shaped electrode 15 and second comb-shaped electrode 16 in place of first interdigital arrangement 9 and second interdigital arrangement 11, respectively.

Figure 13:
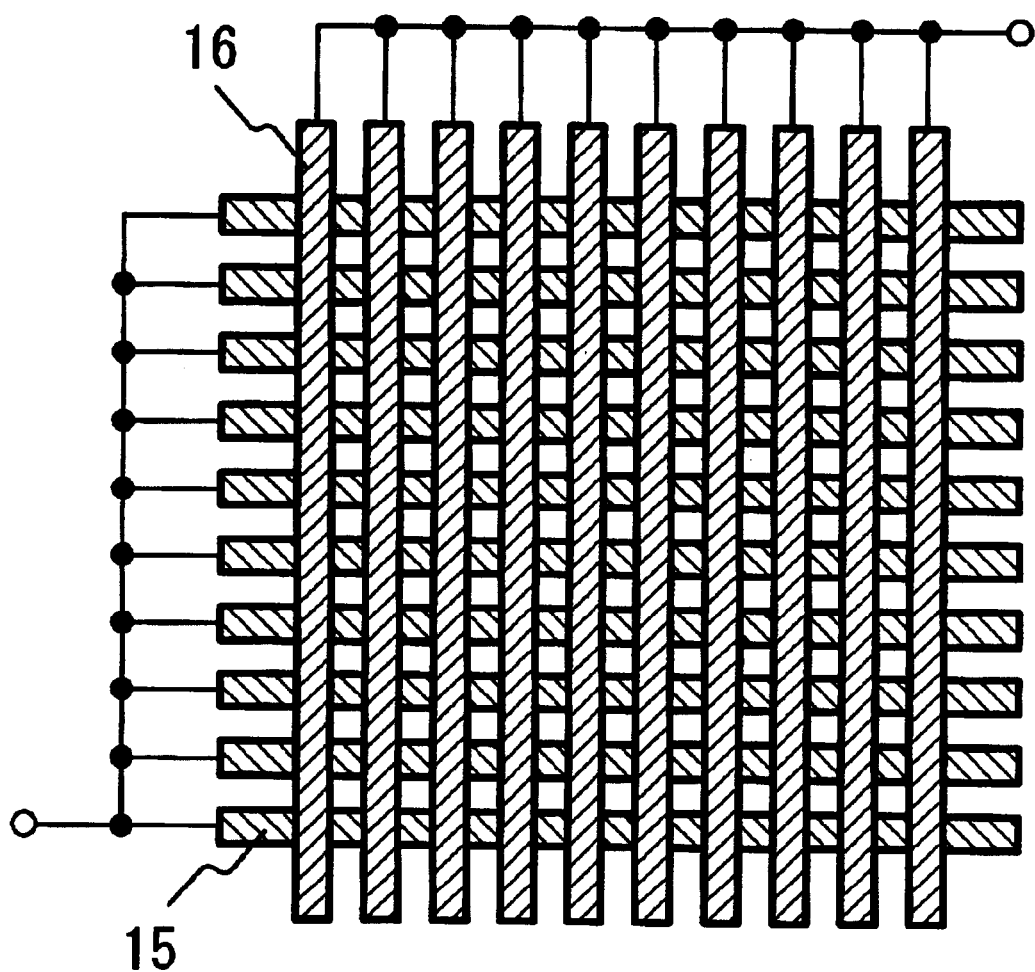
FIG. 13 shows a schematic illustration of first comb-shaped electrode 15 and second comb-shaped electrode 16.

FIG. 13 shows a schematic illustration of first comb-shaped electrode 15 and second comb-shaped electrode 16. First comb-shaped electrode 15 has forty electrode-fingers, a finger-overlap length (L) of 5 mm, a finger width (W) of 175 μm, and an interdigital periodicity (P) of 225 μm. Second comb-shaped electrode 16 has the same construction pattern as first comb-shaped electrode 15, of which the finger direction is orthogonal to that of second comb-shaped electrode 16.

In the device for measuring sound velocity in material in FIG. 12, if input electric signals with a frequency f, respectively, are applied between first comb-shaped electrode 15 and counter electrode 3 from signal generator 4 in turn, longitudinal waves along the direction vertical to the lower end surface of first piezoelectric substrate 8 are radiated into the material through silicone rubber 12. When the material is water, the condition of $P/T<4V_w/V_s$ enables a radiation of the longitudinal waves along the direction vertical to the lower end surface of first piezoelectric substrate 8 into water.

If the longitudinal waves are reflected at reflector 7 as shown in FIG. 12, reflected longitudinal waves are detected between second comb-shaped electrode 16 and counter electrode 3 as the delayed electric signals $D_i$ in accordance with the distances $Z_i$, respectively. On the other hand, electrical coupled-signals from the input electric signals applied between first comb-shaped electrode 15 and counter electrode 3 are also detected between second comb-shaped electrode 16 and counter electrode 3. The electrical coupled-signals and the delayed electric signals $D_i$ interfere respectively with each other, so that the respective interference signals $R_i$ are detected at signal analyzer 5. Tracing a dependence of respective amplitudes of the interference signals $R_i$ on the distances $Z_i$ provides a distance periodicity ΔZ. Thus, a sound velocity V in the material is calculated from the product of twice the frequency f and the distance periodicity ΔZ, that is, V=2fΔZ.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A device for measuring sound velocity in material comprising:

a piezoelectric substrate;

a first comb-shaped electrode formed on an upper end surface of said piezoelectric substrate;

a second comb-shaped electrode formed on said upper end surface of said piezoelectric substrate;

a counter electrode formed on a lower end surface of said piezoelectric substrate and in contact with a surface-part of a material;

a reflector parallel with said lower end surface of said piezoelectric substrate and in contact with the opposite surface-part of said material;

a distance adjusting system adjusting distances $Z_i$ (i=1, 2, ..., n) between said surface-part and said opposite surface-part of said material in turn; and a signal analyzer, said first- and second comb-shaped electrodes forming an interdigital arrangement, said first comb-shaped electrode and said counter electrode receiving input electric signals with a frequency f, respectively, radiating longitudinal waves into said material along the direction vertical to said lower end surface of said piezoelectric substrate, and making said reflector reflect said longitudinal waves back, said second comb-shaped electrode and said counter electrode detecting electrical coupled-signals from said input electric signals, respectively, as well as reflected longitudinal waves as delayed electric signals $D_i$ (i=1, 2, . . . , n) in accordance with said distances $Z_i$, said signal analyzer causing said electrical coupled-signals and said delayed electric signals $D_i$ to interfere respectively, making respective interference signals $R_i$ (i=1, 2, . . . , n), detecting respective amplitudes of said interference signals $R_i$, clarifying a distance periodicity $\Delta Z$ from a dependence of said amplitudes on said distances $Z_i$, and calculating a sound velocity V in said material from the product of twice said frequency f and said distance periodicity $\Delta Z$.

2. A device for measuring sound velocity in material as defined in claim 1, wherein the ratio of the interdigital periodicity of said interdigital arrangement to the thickness of said piezoelectric substrate is smaller than four times the ratio of the longitudinal wave velocity in said material to the longitudinal wave velocity in said piezoelectric substrate.

3. A device for measuring sound velocity in material as defined in claim 1, wherein said interdigital arrangement has a large number of electrode-finger pairs, and causes a structure with a large number of electrode-fingers in said first comb-shaped electrode, said structure making the directionality in radiation of said longitudinal waves into said material more sharply than another structure with a smaller number of electrode-fingers if said structure has a condition that the total amount of all the finger-areas of said first comb-shaped electrode is the same as that for said another structure.

4. A device for measuring sound velocity in material as defined in claim 1, wherein said piezoelectric substrate is made of a piezoelectric ceramic plate, the polarization axis thereof being parallel to the thickness direction thereof.

5. A device for measuring sound velocity in material as defined in claim 1, wherein said material is a liquid matter.

6. A device for measuring sound velocity in material as defined in claim 1, wherein said material is a cellular tissue.

7. A device for measuring sound velocity in material as defined in claim 1 further comprising a polymer film, with which said lower end surface of said counter electrode is coated.

8. A device for measuring sound velocity in material as defined in claim 1 further comprising a silicone rubber, with which said lower end surface of said counter electrode is coated.

9. A device for measuring sound velocity in material comprising:

a first piezoelectric substrate;

a first interdigital arrangement of two comb-shaped electrodes formed on a lower end surface of said first piezoelectric substrate, a lower end surface of said first interdigital arrangement being in contact with a surface-part of a material;

a second piezoelectric substrate;

a second interdigital arrangement of two comb-shaped electrodes formed on an upper end surface of said second piezoelectric substrate;

a counter electrode cemented between said first- and second piezoelectric substrates;

a reflector parallel with said lower end surface of said first piezoelectric substrate and in contact with the opposite surface-part of said material;

a distance adjusting system adjusting distances $Z_i$ (i=1, 2, . . . , n) between said surface-part and said opposite surface-part of said material in turn; and a signal analyzer, one of said two comb-shaped electrodes in said first interdigital arrangement and said counter electrode receiving input electric signals with a frequency f, respectively, radiating longitudinal waves into said material along the direction vertical to said lower end surface of said first piezoelectric substrate, and making said reflector reflect said longitudinal waves back, one of said two comb-shaped electrodes in said second interdigital arrangement and said counter electrode detecting electrical coupled-signals from said input electric signals, respectively, as well as reflected longitudinal waves as delayed electric signals $D_i$ (i=1, 2, . . . , n) in accordance with said distances $Z_i$, said signal analyzer causing said electrical coupled-signals and said delayed electric signals $D_i$ to interfere respectively, making respective interference signals $R_i$ (i=1, 2, . . . , n), detecting respective amplitudes of said interference signals $R_i$, clarifying a distance periodicity $\Delta Z$ from a dependence of said amplitudes on said distances $Z_i$, and calculating a sound velocity V in said material from the product of twice said frequency f and said distance periodicity $\Delta Z$.

10. A device for measuring sound velocity in material as defined in claim 9, wherein the finger direction of said second interdigital arrangement is orthogonal to that of said first interdigital arrangement.

11. A device for measuring sound velocity in material as defined in claim 9, wherein the finger width in said one of said two comb-shaped electrodes in said first interdigital arrangement is wider than that in the other of said two comb-shaped electrodes in said first interdigital arrangement, and the finger width in said one of said two comb-shaped electrodes in said second interdigital arrangement is wider than that in the other of said two comb-shaped electrodes in said second interdigital arrangement.

12. A device for measuring sound velocity in material as defined in claim 9, wherein the ratio of the interdigital periodicity of said first interdigital arrangement to the thickness of said first piezoelectric substrate is smaller than four times the ratio of the longitudinal wave velocity in said material to the longitudinal wave velocity in said first piezoelectric substrate.

13. A device for measuring sound velocity in material as defined in claim 9, wherein said first interdigital arrangement has a large number of electrode-finger pairs, and causes a structure with a large number of electrode-fingers in one of said two comb-shaped electrodes in said first interdigital arrangement, said structure making the directionality in radiation of said longitudinal waves into said material more sharply than another structure with a smaller number of electrode-fingers if said structure has a condition that the total amount of all the finger-areas of said one of said two comb-shaped electrodes in said first interdigital arrangement is the same as that for said another structure.

14. A device for measuring sound velocity in material comprising:

a first piezoelectric substrate;

a first comb-shaped electrode formed on a lower end surface of said first piezoelectric substrate, a lower end surface of said first comb-shaped electrode being in contact with a surface-part of a material;

a second piezoelectric substrate;

a second comb-shaped electrode formed on an upper end surface of said second piezoelectric substrate;

a counter electrode cemented between said first- and second piezoelectric substrates;

a reflector parallel with said lower end surface of said first piezoelectric substrate and in contact with the opposite surface-part of said material;

a distance adjusting system adjusting distances $Z_i$ (i=1, 2, . . . , n) between said surface-part and said opposite surface-part of said material in turn; and a signal analyzer, said first comb-shaped electrode and said counter electrode receiving input electric signals with a frequency f, respectively, radiating longitudinal waves into said material along the direction vertical to said lower end surface of said piezoelectric substrate, and making said reflector reflect said longitudinal waves back, said second comb-shaped electrode and said counter electrode detecting electrical coupled-signals from said input electric signals, respectively, as well as reflected longitudinal waves as delayed electric signals $D_i$ (i=1, 2, . . . , n) in accordance with said distances $Z_i$, said signal analyzer causing said electrical coupled-signals and said delayed electric signals $D_i$ to interfere respectively, making respective interference signals $R_i$ (i=1, 2, . . . , n), detecting respective amplitudes of said interference signals $R_i$, clarifying a distance periodicity $\Delta Z$ from a dependence of said amplitudes on said distances $Z_i$, and calculating a sound velocity V in said material from the product of twice said frequency f and said distance periodicity $\Delta Z$.

15. A device for measuring sound velocity in material as defined in claim 14, wherein the finger direction of said second comb-shaped electrode is orthogonal to that of said first comb-shaped electrode.

16. A device for measuring sound velocity in material as defined in claim 14, wherein the ratio of the interdigital periodicity of said first comb-shaped electrode to the thickness of said first piezoelectric substrate is smaller than four times the ratio of the longitudinal wave velocity in said material to the longitudinal wave velocity in said first piezoelectric substrate.

17. A device for measuring sound velocity in material as defined in claim 14, wherein said first comb-shaped electrode has a structure with a large number of electrode-fingers, said structure making the directionality in radiation of said longitudinal waves into said material more sharply than another structure with a smaller number of electrode-fingers if said structure has a condition that the total amount of all the finger-areas of said first comb-shaped electrode is the same as that for said another structure.

* * * * *